United States Patent
Renard et al.

(10) Patent No.: US 7,893,316 B1
(45) Date of Patent: Feb. 22, 2011

(54) METHOD FOR RECONSTRUCTING A NON-HUMAN MAMMAL EMBRYO WITH FOETAL ADULT DIFFERENTIATED CELLS

(75) Inventors: Jean-Paul Renard, Vanves (FR); Xavier Vignon, Versailles (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 738 days.

(21) Appl. No.: 10/089,454

(22) PCT Filed: Sep. 29, 2000

(86) PCT No.: PCT/FR00/02698

§ 371 (c)(1),
(2), (4) Date: Jan. 5, 2004

(87) PCT Pub. No.: WO01/24624

PCT Pub. Date: Apr. 12, 2001

(30) Foreign Application Priority Data

Oct. 1, 1999 (FR) .................................. 99 12287

(51) Int. Cl.
*C12N 15/00* (2006.01)
*A01K 67/027* (2006.01)

(52) U.S. Cl. .............................. 800/24; 800/14; 800/15; 800/16; 800/17; 800/18

(58) Field of Classification Search .................... 800/24
See application file for complete search history.

(56) References Cited

U.S. PATENT DOCUMENTS 6,753,457 B2 * 6/2004 Wangh ........................ 800/24

OTHER PUBLICATIONS

Aaronson et al. JCB 62:746-754 (1974).*
Samocha-Bone, D et al, 1998, Molec. Human Reprod., 4:133-137.*
Delgado et al, 2001, Arch Androl, 47:47-58.*
Reyes et al, Gamete Res, 1989, 23:39-47.*
Lassale et al., J. Reprod. Fert., 1992, 95:313-324.*
Adenot et al., 1997, Development, 124: 4615-4625.
Brown et al., 1977, Experimental Cell Research, 104: 207-213.
Campbell et al., 1993, Biology of Reproduction, 49: 933-942.
Kraemer et al., 1970, Biochim. Biophys. Acta., 224: 568-578.
Liu et al., 1998, Molecular Reproduction and Development, 49: 298-30.
Renard et al., 1999, Lancet., 353: 1489-1491.
Sun et al., 1995, Current Topics in Developmental Biology, 30: 147-176.
Vignon et al., 1999, Theriogenology, 51: 216.
Vignon et al., 1998, C.R. Acad. Sci. Paris Sciences de la vie/Life Sciences, 321: 735-745.

* cited by examiner

*Primary Examiner*—Valarie Bertoglio
(74) *Attorney, Agent, or Firm*—Morgan, Lewis & Bockius LLP

(57) ABSTRACT

The invention concerns the reconstruction in vitro of non-human mammal embryos by a method which consists in treating the nucleus of a somatic donor cell prior to its transfer into a receiver cytoplasm, said treatment comprising controlled proteolysis of non-histone proteins, and inducing an isomorphic swelling of said nucleus.

12 Claims, No Drawings

METHOD FOR RECONSTRUCTING A NON-HUMAN MAMMAL EMBRYO WITH FOETAL ADULT DIFFERENTIATED CELLS

The present invention relates to the reconstitution of mammalian embryos by nuclear transfer.

Techniques for producing animals, in particular mammals, from embryos reconstituted by transferring the nucleus of a somatic donor cell into the cytoplasm of a recipient cell (generally an oocyte) enucleated beforehand are currently the subject of great interest due to their potential applications. Among the latter, mention may be made in particular of:

- animal transgenesis: the integration of a gene of interest into cells in culture, followed by the transfer of the nuclei thereof into recipient oocytes could make it possible to increase the efficiency of transgenesis;
- the possibility of multiplying animals having particular genetic characteristics, whether these characteristics are natural or result from transgenesis;
- genetic evaluation: the fact of having several animals possessing an identical genetic inheritance may make it possible to evaluate the respective influence of genetic and environmental factors on the qualities of an animal;
- the possibility of obtaining embryonic cell lines which can then be differentiated in vitro.

The main obstacles encountered in developing techniques for reconstituting an embryo by nuclear transfer come from the difficulty in coordinating the donor nucleus/recipient cytoplasm interactions on which the future development of the embryo depends.

Methods for nuclear transfer therefore conventionally comprise, prior to the nuclear transfer, the preparation of the donor cell and/or of the recipient cell.

The recipient cells generally used result from the enucleation of oocytes at the metaphase II stage, after maturation in vitro. At this stage of the cell cycle, the cytoplasm has considerable MPF (Maturation Promoting Factor) activity, which gradually decreases from the time at which the cytoplasm is activated. This activation, which results from the entry of a spermatozoon in the case of natural fertilization, may be artificially induced in the case of transfer of the nucleus.

When the transfer of the nucleus and the activation of the recipient cytoplasm occur simultaneously (which happens, for example, when the fusion of the nucleus and the cytoplasm is effected by an electrical pulse sufficient to stimulate the latter), the high MPF activity induces degradation of the nuclear envelope, the chromatin condensation exposing, immediately after fusion, the nuclear material to a metaphase cytoplasmic environment. It has been reported [CAMPBELL et al., Biol. Reprod., 49, 933-942, (1993)] that these phenomena risk causing chromosomal abnormalities, in particular when the donor nucleus is in the G2 or S phase of the cell cycle.

In order to avoid premature condensation of the chromatin and to keep the nuclear envelope intact, it has been proposed [BARNES et al., Mol. Reprod. Dev., 36, 33-41, (1993); STICE et al., Mol. Reprod. Dev., 38, 61-68, (1994)] to pre-activate the recipient cytoplasm and to carry out the transfer of the nucleus only when a cytoplasmic environment of the interphase type has been obtained, which in particular results in a low level of MPF activity, or to use a recipient cytoplasm originating from old oocytes (CHESNE et al., CRAS, 316, 487-492, (1993)], which are more sensitive to activation and in which the transition to the interphase occurs more rapidly.

This approach makes it possible to improve success rates when embryonic cells (blastomers) are used as donor cells. On the other hand, in particular in Bovini, it is much less efficient in the case of nuclei originating from nuclei of differentiated somatic cells, in which the rates of embryo development remain very low [VIGNON et al., C.R. Acad. Sci. Paris, 321, 735-745, (1998); RENARD et al., The Lancet, 353, 1489-1491, (1999)].

According to another approach, exposure of the donor nucleus derived from a differentiated cell to the factors of the recipient cytoplasm in metaphase would have the effect of allowing reprogramming of the nucleus, and of restoring its totipotency. PCT International Application WO 97/07668, in the name of the ROSLIN INSTITUTE (inventors: WILMUT et al.) thus proposes only activating the oocytes several hours after fusion, in order to prolong the contact between the nuclear material derived from the donor cell and the recipient cytoplasm. In order to maintain correct ploidy under these conditions, it is necessary to use donor cells in the G0 or G1 phase, and to stabilize or inhibit the microtubule formation during activation.

PCT International Application WO 97/07669, in the name of the ROSLIN INSTITUTE (inventors: WILMUT et al.) recommends the use of nuclei obtained from cells taken to the quiescent state ($G_0$ phase of the cell cycle) beforehand by a period of culturing in the absence of serum; this treatment is also thought to facilitate the reprogramming of the donor nucleus, by making it more receptive to cytoplasmic factors from the recipient cell. This approach has made it possible, in particular in the ovine race, to improve the rate of development of embryos obtained from nuclei of differentiated cells.

In mice, WAKAMAYA et al. (Nature, 394, 369-374, 1998) report the development of embryos obtained from nuclei, in the $G_0$ or $G_1$ phase, of differentiated cumulus cells, injected into the cytoplasm of oocytes in metaphase II activated 1 to 3 hours after injection.

The inventors have now developed a novel method for reconstituting mammalian embryos in vitro, which makes it possible to improve the rates of production and of development of viable embryos from nuclei of somatic cells derived from various fetal or adult tissues.

This method comprises treating the diploid nucleus of a somatic cell prior to its transfer into a recipient cytoplasm, said treatment comprising:

a) controlled proteolysis of non-histone proteins, and
b) induction of an isomorphic swelling of said nucleus.

The effect of this treatment is to make the nuclear DNA more accessible and more reactive to the cytoplasmic environment in which there are factors capable of interacting with the structures of the nucleus even when there is no rupturing of the nuclear envelope [ADENOT et al., Development, 124, 4615-4625, (1997); THOMPSON et al., Dev. Genetics, 42, 22-31, (1998)]. The preservation of the nuclear membrane allows correct ploidy to be maintained before the first division of the embryo.

The diploid nucleus may in particular be obtained from primary cultures of fetal cells or of adult cells originating from various tissues (for example mammary gland or skin epithelia, muscle cells, hepatic cells, etc.). The cells may be indifferently derived from a fresh primary culture, or from a culture established over several passages or reinitiated from cells preserved by freezing. The cells may be used no matter what phase of the cell cycle they are in.

The nuclei may be removed from these donor cells, treated in accordance with the invention, and then transferred by microinjection into the recipient cytoplasm; it is, however, more convenient, in practice, to treat the nuclei contained in the donor cells and to then carry out the nuclear transfer by fusion of the donor cell and of the recipient cytoplasm.

In the latter case, the implementation of the method of the invention requires a prior step of permeabilization of the cytoplasmic membrane of the donor cell in order to make the nucleus accessible to the action of the treatments.

The permeabilization of the plasma membranes may, for example, be obtained by incubating the cell with one or more gentle permeabilizing agents, such as lysolecithin, streptolysin, saponin or digitonin, on condition that the conditions for use do not induce cell lyses and preserve the plasma membrane in a state compatible with the subsequent operation of fusion with the recipient oocyte. The doses which can be used and the incubation conditions vary from one source of cells to the other. Suitable conditions are determined by testing the permeabilization beforehand using Trypan blue; permeabilized cells become blue in color, which can be easily observed under the microscope. Suitable conditions correspond to those which give between 50 and 100% of permeable cells. The permeabilization treatment is carried out simultaneously with the proteolysis and prior to inducing the swelling of the nuclei, which requires a longer incubation.

For the controlled proteolysis, use will be made of a serine protease, such as trypsin or chymotrypsin; the action of the protease must be limited to the degradation of non-histone proteins of the nucleus, and of proteins of the cytoskeleton surrounding the nucleus, and must not lead to lysis of the nuclei. Generally, very low protease concentrations will be used. For example, in the case of proteolysis performed on whole cells (at the same time as the permeabilization or consecutively thereto), trypsin concentrations of the order of 1 to 10 U/ml may be used in the cell incubation mixture, for an incubation duration ranging from 1 to 10 min at 37° C. In the case of treatment of isolated nuclei, the protease doses and the incubation times must be reduced further.

In addition, the trypsin has a direct activation effect on DNA polymerases in the cells which are in the G1 or G0 phase during the treatment [BROWN et al., Exp. Cell Res., 104, 207-213, (1977)]. This would make it possible to facilitate the resumption of the cell cycle of the nuclei which are in the G0/G1 phase when they are incorporated into a recipient cytoplasm in the interphase.

The swelling of the nucleus may be induced by treatment with at least one polyanionic compound, such as heparin, dextran sulfate or high molecular weight ($\geq$20,000 Da) polyaspartic acids, as described by KRAEMER and COFFEY [Biochim. Biophys. Acta., 224, 568-578 (1970)].

The treatment is carried out, after the proteolysis or simultaneously therewith, by incubating the nuclei, or the cells containing them, in the presence of the polyanion until swelling of the nucleus is observed. For example, in the case of permeabilized whole cells, between 50 and 200 µg of polyanion per ml of incubation medium may be used, for an incubation of 30 to 60 min at room temperature (15 to 25° C.).

At the end of this treatment, the nucleus is transferred into the recipient cytoplasm.

The transfer of the nuclei treated in accordance with the invention may be carried out whatever the stage of the cell cycle of the donor cells and whatever the state of the recipient cytoplasm. In the case of fusion of the nuclei with recipient oocytes in metaphase II (20 to 25 h after the start of maturation), it will be necessary to activate the reconstituted embryos, for example by a process of chemical activation as has been described by LIU et al. [Mol. Reprod. Dev., 49, 298-307, (1998)], or by any other method.

It is, however, particularly advantageous to use recipient cytoplasms which have been prepared beforehand so as to take them to interphase.

A "recipient cytoplasm in interphase" is defined as a cytoplasm in which the level of MPF is less than that at which it induces degradation of the nuclear membrane and chromatin condensation.

This cytoplasm may in particular be obtained from an oocyte matured in vivo or in vitro. The chromosomal material is withdrawn by micromanipulation, while the oocyte is blocked in the metaphase II stage. The resulting cytoplasm is then treated to decrease the MPF activity. It may, for example, be prepared by a method of in vitro aging and cooling before fusion [CHESNE et al., C. R. Acad. Sci., 316, 487-491, (1993)]. It is also possible to obtain the same result using drugs which inhibit protein synthesis (cycloheximide) or drugs which inhibit phosphorylation (6-DMAP), or a mixture of the 2 drugs. In this case, the interphase state is generally obtained in 1 to 4 h of incubation.

The embryo may be reconstituted, in the case of isolated nuclei, by microinjection. It is, however, particularly advantageous to directly use cells treated in order to fuse them with the recipient cytoplasms. In this case, the fusion is preferably carried out by electric shock, or by any other method. It is not necessary to operate under conditions intended to induce activation of the recipient cytoplasm.

The reconstituted embryos are directly cultured in vitro without any other activation after the fusion; until they develop to the blastocyst stage.

The donor nuclei do not undergo any destruction of their nuclear membrane, nor any chromatin condensation (PCC) before the first division which occurs after the fusion.

When the embryos have reached the blastocyte stage, they are then transferred into recipient females, according to conventional techniques known per se.

The method in accordance with the invention makes it possible, firstly, to improve the reprogramming of the nuclei transferred by allowing access of the cytoplasmic factors to the chromatin by virtue of moderate enzymatic action before the fusion and, secondly, to promote maintenance of correct ploidy of the embryonic cells by minimizing the chromatin condensation and preventing its dispersion during the remodeling of the nucleus introduced into the recipient cytoplasm. This modification in the initial steps of the relationships between the nucleus and the cytoplasm makes it possible to promote the eventual development of the embryos reconstituted from nuclei of differentiated somatic cells, this being no matter what phase of the cell cycle these cells are in.

It may apply to various mammalian species; it is, however, more particularly suitable for reconstituting embryos of ungulate mammals, especially of ruminants, and in particular of the ovine race, of Bovini, of members of the goat family or of pigs.

The present invention will be more clearly understood from the further description which follows, which refers to nonlimiting examples of implementation of the process in accordance with the invention, for reconstituting bovine embryos.

EXAMPLE 1

Preparation of the Cells and Reconstitution of the Embryos

The donor cells are obtained from fetal skin or muscle cell cultures, or from ear biopsy cultures from adult animals (skin cells), prepared as described by VIGNON et al., (C. R. Acad. Sci. Paris, 321, 735-745, 1998). Under these conditions, differentiated cells of the fibroblast type are obtained.

The culture medium is removed from the dishes of cells, which are rinsed with PBS buffer and filled with a "permeabilization" medium, the composition of which is as follows: HANKS balanced salt solution without calcium and magnesium, containing 0.5 µg/ml of trypsin, and 20 to 30 µg/ml of lysolecithin in the case of the fetal skin cells and 15 to 20 µg/ml of lysolecithin in the case of the skin cells from adult animals. After incubation for 5 min at 37° C., the incubation medium is removed from the dishes. To stop the permeabilization and proteolysis, the dishes are immediately rinsed with a buffer solution (HANKS balanced salt solution without calcium and magnesium) containing 0.5% of fetal calf serum or of bovine serum albumin.

The dishes are then filled with a "polyanionic" medium with the following composition: HANKS solution without calcium and magnesium, containing 10 U/ml of heparin. The incubation is carried out for 30 to 60 min at room temperature. The cells are then collected by scraping the culture support, centrifuged at 1 200 g for 5 min and resuspended in serum-free culture medium prior to the fusion with the recipient oocytes.

The recipient oocytes are enucleated, and taken to interphase according to the protocol described by VIGNON et al. [C. R. Acad. Sci. Paris, 321, 735-745, (1998)].

The nuclear transfer is performed by introducing an isolated donor cell under the zona pellucida of the recipient cytoplasm and performing the fusion under the following conditions: 2 electrical pulses of 2.2 kV/cm, lasting 20 µs, in TCM199 medium (LIFE TECHNOLOGIES, Cergy Pontoise, France) supplemented with 5 µg/ml of cytochalasin B.

Fusion is verified by observation with a binocular microscope, and the reconstituted embryos are cultured in vitro, and them implanted in vivo, as described by VIGNON et al. [C. R. Acad. Sci. Paris, 321, 735-745, (1998)].

Controls:

Controls are obtained according to the protocol described above, but with neither permeabilization nor trypsin and heparin treatment of the donor cells.

Results:

In the case of the fetal cells, from skin or from muscle, 47 blastocysts were obtained after having reconstituted 663 embryos (7.1%) with donor cells having undergone the treatment in accordance with the invention. By comparison, with the control cells, 13 blastocysts were obtained for 386 reconstituted embryos (3.37%).

After transplantation of the embryos obtained from the donor cells having undergone the treatment in accordance with the invention, 27 recipient cows gave 5 gestations of more than 90 days and 4 viable animals were produced. For the control cells, 6 recipient cows were transplanted and only one gestation went beyond 90 days, but without reaching full term (late abortion at 8 months of gestation).

In the case of the cells derived from ear biopsies from adult animals, 23 blastocysts were produced after 580 embryo reconstructions (4%) with donor cells having undergone the treatment in accordance with the invention, whereas 6 blastocysts were obtained out of 250 reconstructions (2.4%) with control cells. All the embryos were transplanted, and one birth was obtained, from the series of embryos derived from treated cells.

EXAMPLE 2

In another series of experiments, embryos were reconstituted, according to the protocol described in example 1 above, from fetal or adult bovine somatic cells derived from proliferating cultures, or derived from cultures placed in a state of quiescence (by maintaining them in a serum-free medium for the 36 to hours preceding their use). Control embryos were also reconstituted as described in example 1 above.

The results are illustrated by tables I and II below. Table I represents the results obtained with the donor cells derived from proliferating cultures.

TABLE I

| Donor cells | Number of embryos Reconstituted (%) | Cleaved (%) | Number of morulae (%) | Number of Blastocysts (%) |
|---|---|---|---|---|
| Treated | 502 (56.5) | 256 (51.0) | 43 (8.6) | 28 (5.6) |
| Controls | 221 (55.6) | 115 (52.0) | 10 (4.5) | 6 (2.7) |

Table II represents the results obtained with the quiescent donor cells.

TABLE II

| Donor cells | Number of embryos Reconstituted (%) | Cleaved (%) | Number of Morulae (%) | Number of Blastocysts (%) |
|---|---|---|---|---|
| Treated | 717 (58.9) | 337 (47.0) | 83 (11.6) | 48 (6.7) |
| Controls | 280 (69.3) | 168 (60.0) | 13 (4.6) | 7 (2.5) |

These results show that, in the context of the use of a recipient cytoplasm in interphase, the initial state of the donor cells (quiescence or proliferation) has no significant influence on the rate of embryo development; on the other hand, the treatment of the donor cells in accordance with the invention significantly increases this rate of development.

The blastocysts obtained at the end of the 2 experiments above were transferred into recipient cows. The results are illustrated by table III below.

TABLE III

| Cells | Number of blastocysts transferred | Number of gestations/number of recipients | | | Births |
|---|---|---|---|---|---|
| | | D 35 | D 60 | D > 90 | |
| Treated | 76 | 7/50 (14.0) | 6/50 (12.0) | 6/50 (12.0) | 5 (10.0) |
| Non-treated | 13 | 3/8 (37.5) | 1/8 (12.5) | 1/8 (12.5) | 0 (0.0) |

These results confirm that the treatment of the donor cells in accordance with the invention significantly increases the rate of production of embryos which may give rise to viable animals.

EXAMPLE 3

The donor cells are proliferating fibroblasts derived from culturing fetal or adult bovine skin cells. They are prepared as in example 1. The permeabilization is carried out by incubation in the presence of 15 to 20 µg/ml of lysolecithin.

The recipient oocytes are enucleated after 22 to 24 h of maturation in vitro and fused at 24-25 h with the donor cells under the same conditions as those described in example 1. The fusion is followed by chemical activation according to a protocol described by LIU et al. [Mol. Reprod. Dev., 49, 298-307, (1998)]: immediately after fusion, the reconstituted embryos are incubated in the presence of 10 µg/ml of cycloheximide and 5 µg/ml of cytochalasin B in TCM 199 medium (LIFE TECHNOLOGIES, Cergy Pontoise, France) for 5 h. The embryos are then cultured in vitro. Control embryos were reconstituted in the same way, but without treatment of the donor cells prior to fusion.

The results are illustrated by tables IV and V below:

TABLE IV

| Donor cells | Reconstituted embryos (%) | Cleaved embryos (%) | Morulae (%) | Blastocysts (%) |
|---|---|---|---|---|
| Treated | 365 (53.7) | 227 (62.2) | 101 (27.7) | 88 (24.1) |
| Controls | 438 (59.2) | 271 (61.9) | 101 (21.1) | 70 (16.0) |

TABLE V

| Donor cells | Blastocysts transferred | Gestation/ rec D 35 | Gestation/ rec D 60 | Gestation/ rec D 90 | Births |
|---|---|---|---|---|---|
| Treated | 60 | 18/40 (45.0) | 17/40 (42.5) | 9/40 (22.5) | 4/40 (10.0) |
| Controls | 55 | 10/38 (26.3) | 8/38 (21.0) | 4/38 (10.5) | 2/38 (5.3)+ |

+: these two animals died a few hours after birth

The invention claimed is:

1. A method for reconstituting a non-human mammalian embryo in vitro, wherein said method consists of:
   (i) treating a non-human mammal diploid nucleus of a somatic donor cell, said treatment consisting of:
      a) controlled proteolysis of nuclear non-histone proteins and surrounding cytoskeleton proteins of the nucleus, wherein the controlled proteolysis must not cause lysis of the nucleus; and
      b) induction of an isomorphic swelling of the nucleus after controlled proteolysis of step a), by treatment consisting of treating with a polyanion; and
   (ii) transferring said treated nucleus into the cytoplasm of a recipient oocyte during metaphase II or interphase, wherein the recipient oocyte is enucleated thereby forming a nuclear transfer unit; and
   (iii) activating the nuclear transfer unit when the recipient oocyte is in metaphase II, thereby reconstituting an embryo;
wherein said reconstituted embryo undergoes cell division directed by said treated nucleus.

2. The method of claim 1, wherein the controlled proteolysis is produced by the action of a serine protease.

3. The method of claim 2, wherein the serine protease is trypsin or chymotrypsin.

4. The method of claim 1, said polyanion is selected from the group consisting of polyaspartic acids having a molecular weight of greater than 20,000 Da, heparin, and dextran sulfate.

5. The method of claim 1, wherein the treated nucleus is contained in the donor cell, and the treatment comprises permeabilization of the cytoplasmic membrane of said cell.

6. The method of claim 5, wherein permeabilization of the cytoplasmic membrane is carried out with at least one permeabilizing agent selected from the group consisting of lysolecithin, streptolysin, saponin and digitonin.

7. The method of claim 1, wherein the nucleus is transferred into the recipient cytoplasm by microinjection.

8. The method of claim 5, wherein the nucleus is transferred into the recipient cytoplasm by fusion of the donor cell and of the recipient cytoplasm.

9. The method of claim 8, wherein the fusion is carried out by electric shock.

10. The method of claim 1, wherein the recipient cytoplasm is in the interphase state.

11. The method of claim 1, wherein said mammal is an ungulate.

12. The method of claim 11, wherein the ungulate is selected from the group consisting of bovine, ovine, caprine, and porcine.

* * * * *